(12) United States Patent
Pang et al.

(10) Patent No.: US 10,040,824 B2
(45) Date of Patent: Aug. 7, 2018

(54) FLAVIVIRUS VACCINE

(75) Inventors: Xiaowu Pang, Rockville, MD (US); Xinbin Gu, Rockville, MD (US)

(73) Assignee: Tengen Biomedical Company, Bethesda, MD (US)

( * ) Notice: Subject to any disclaimer, the term of this patent is extended or adjusted under 35 U.S.C. 154(b) by 318 days.

(21) Appl. No.: 11/622,233

(22) Filed: Jan. 11, 2007

(65) Prior Publication Data

US 2007/0249032 A1 Oct. 25, 2007

Related U.S. Application Data

(63) Continuation of application No. PCT/US2005/024428, filed on Jul. 11, 2005.

(60) Provisional application No. 60/586,722, filed on Jul. 12, 2004.

(51) Int. Cl.

| | |
|---|---|
| *C07K 14/005* | (2006.01) |
| *C12N 7/00* | (2006.01) |
| *C12N 15/86* | (2006.01) |
| *A61K 39/00* | (2006.01) |

(52) U.S. Cl.
CPC .............. *C07K 14/005* (2013.01); *C12N 7/00* (2013.01); *C12N 15/86* (2013.01); *A61K 2039/5254* (2013.01); *A61K 2039/5258* (2013.01); *C12N 2770/24123* (2013.01); *C12N 2770/24134* (2013.01); *C12N 2770/24143* (2013.01); *Y02A 50/386* (2018.01); *Y02A 50/388* (2018.01); *Y02A 50/39* (2018.01); *Y02A 50/394* (2018.01)

(58) Field of Classification Search
USPC ........................................................ 435/235
See application file for complete search history.

(56) References Cited

U.S. PATENT DOCUMENTS

| | | |
|---|---|---|
| 2004/0265338 A1 | 12/2004 | Pang et al. |
| 2009/0155301 A1 | 6/2009 | Mason et al. |

FOREIGN PATENT DOCUMENTS

| | | | | |
|---|---|---|---|---|
| WO | WO9837911 | * | 9/1998 | |
| WO | WO 99/28487 | * | 6/1999 | ............. C12N 15/86 |
| WO | WO9928487 | * | 6/1999 | |
| WO | WO 02/072803 | * | 9/2002 | ............... C12N 7/04 |
| WO | WO02072803 | * | 9/2002 | |
| WO | WO02081754 | * | 10/2002 | |
| WO | WO03043189 | | 6/2003 | |

OTHER PUBLICATIONS

Westaway et al (Virology 234:31-41, 1997).*
Gomez et al (Viral Immunology 16:407-414, Sep. 2003).*
Harvey et al (Journal of Virology 78:531-538, Jan. 2004).*
Shi et al (Virology 296:219-233, 2002).*
Jaaskelainen et al (Journal of Clinical Microbiology41:4336-42, 2003).*
Khromykh et al., "Encapsidation of the flavivirus kunjin replicon RNA by using a complementation system providing kunjin virus structural proteins in trans", 1998, Journal of Virology, 72(7):5967-5977.*
Pang, "Development of Dengue virus type 2 replicons capable of prolonged expression in host cells", 2001, BMC Microbiology, 1(18):pdf pp. 1-7.*
Pang et al., "Development of dengue virus . . . and HIV" BMC Micro 1:28, 2001.
Anraku et al., "Kunjin virus replication . . . Immunity" J Virol 76:3791, 2002.
Khromykh, "Replicon-based . . . viruses" Curr Opin Mol Therap 2:555, 2000.
Varnayski & Khromykh, "Noncytopathic flavivirus . . . genes" Virol 255:366, 1999.
Lo et al., "Potential High-Throughput Assay for Screening Inhibitors of West Nile Virus Replication." Journal of Virology, Dec. 2003, vol. 77, No. 23, pp. 12901-12906.
Corver et al., "Fine Mapping of a cis-Acting Sequence Element in Yellow Fever Virus RNA That Is Required for RNA Replication and Cyclization." Journal of Virology. Feb. 2003, vol. 77, No. 3, pp. 2265-2370.
Khromykh et al., "Encapsidation of the Flavivirus Kunjin Replicon RNA by Using a Complementation System Providing Kunjin Virus Structural Proteins in trans." Journal of Virology. Jul. 1998, vol. 72, No. 7, pp. 5967-5977.
Di Fabio, et al., "Vaginal immunization of Cynomolgus monkeys with *Streptococcus gordonii* expressing HIV-1 and HPV 16 antigens." Vaccine, 1998, vol. 16, No. 5, pp. 485-492.
Castellanos, et al., "Synthetic Peptides Induce a Cytotoxic Response against Human Papillomavirus Type-18." Gynecologic Oncology, 2001, vol. 82, pp. 77-83.
Carrillo et al., "Heterologous Expression of Trypanosoma cruzi trans-Sialidasei n Leishmania major Enhances Virulence." Infection and Immunity, May 2000, vol. 68, No. 5, pp. 2728-2734.
Varnavski, et al., "Stable High-Level Expression of Heterologous Genes In Vitro and In Vitro by Noncytopathic DNA-Based Kunjin Virus Replicon Vectors." Journal of Virology, May 2000, vol. 74, No. 9, pp. 4394-4403.
Pugachev, et al., "Traditional and novel approaches to flavivirus vaccines." International Journal for Parasitology, 2003, vol. 33, pp. 567-582.
Kofler, et al., "Mimicking live flavivirus immunization with a noninfectious RNA vaccine." Institute of Virology, Feb. 2004, vol. 101, No. 7, pp. 1951-1956.
Harvey, et al., "Tetracycline-Inducible Packaging Cell Line for Production of Flavivirus Replicon Particles." Journal of Virology, Jan. 2004, vol. 78, No. 1, pp. 531-538.
Lindenbach et al., "Molecular Biology of Flaviviruses." Advances in Virus Research, vol. 59, pp. 23-61.
Kromykh et al., Efficient trans-complementation of the Flavivirus Kunjin . . . components of the viral replicase. J Virol 73:10272-10280.

* cited by examiner

*Primary Examiner* — Benjamin P Blumel
(74) *Attorney, Agent, or Firm* — MDIP LLC

(57) ABSTRACT

Replicon virus-like particles can be used as *flavivirus* vaccines.

9 Claims, 6 Drawing Sheets

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Peptide insert at residues 109-114 at the
      juncture of the C and prM domains of Dengue virus.
<220> FEATURE:
<221> NAME/KEY: SIGNAL
<222> LOCATION: (1)..(6)
<223> OTHER INFORMATION: Facilitates efficient signal peptidase cleavage
      of the prM protein from its dependence on cleavage in the
      cytoplasm by the viral NS2B-3 protease.

<400> SEQUENCE: 1

Val Pro Gln Ala Gln Ala
1               5
```

FLAVIVIRUS VACCINE

BACKGROUND OF THE INVENTION

Figure 1:
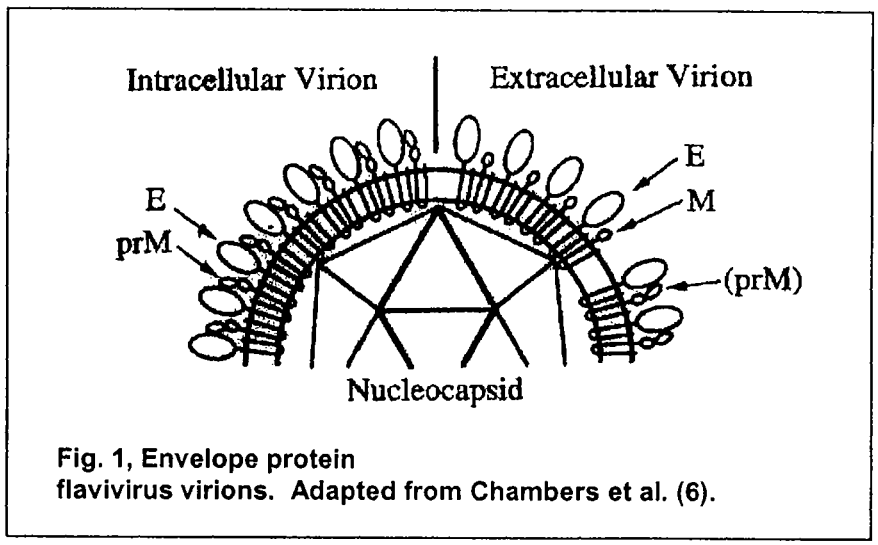
Figure 2:
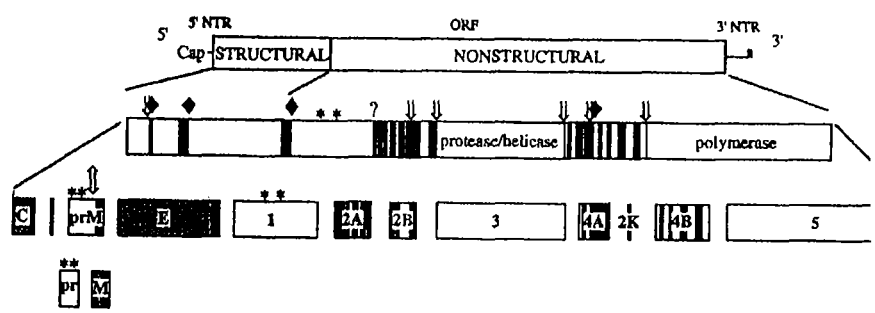

The instant invention relates to the Flaviviridae family of viruses. The *flavivirus* genus includes about 70 members, 40 of which are associated with human illness. The majority of flaviviruses are arboviruses, transmitted to their avian and mammalian hosts, including man, by mosquitoes or ticks. Dengue fever virus (types 1-4), yellow fever virus, Japanese encephalitis virus, tick-borne encephalitis virus and West Nile virus are causative agents of significant morbidity and mortality in human populations. Several flaviviruses, including louping ill that causes neurological disease in sheep, West Nile that causes encephalitis in horse, and Japanese encephalitis that also causes encephalitis in horses as well as stillbirth in domestic pigs, are important veterinary pathogens.

*Flavivirus* genomes consist of a single linear, single-stranded + sense RNA. The + strand is capable of infecting appropriate host cells. The total genome can range from 10 to 11 kbs. There is no 3' polyadenylation. The 5' end has a methylated cap.

*Flavivirus* genomes do not contain internal ribosomal entry sites (IRES) that provide a site of translation initiation for host ribosomes. Instead *flavivirus* employs ribosomal scanning to commence protein synthesis.

*Flavivirus* virions are spheres, 40-65 nm in diameter. Under the lipid envelope is an icosahedral capsid coat approximately 25-30 nm in diameter.

Generally, flaviviruses are transmitted by arthropods, for example, mosquitoes and ticks. Flaviviruses reproduce in their vector organism and are passed from one host to the next.

The yellow fever virus is capable of causing large epidemics. The yellow fever virus is transmitted in monkey and human hosts and in mosquitoes. In the first cycle, the virus is transmitted by *Aedes africanus* and other *Aedes* mosquitoes (in Africa) or by *Hemogogus* mosquitoes (in the Americas); monkeys serve as the reservoir, and generally, humans infected are those who enter deep forests and jungles. In the second cycle, the domestic mosquito, *Aedes aegypti*, which lives in close relationship with humans, may transmit the virus directly to humans, the sole host in the cycle.

The tick-borne encephalitis virus is transmitted by ticks of the genus *Ixodes* in temperate regions of Russia and Europe. The virus can only affect humans in areas where the ticks exist.

Flaviviruses cause other encephalitic diseases, such as, Murray Valley encephalitis, Rocio and Powassan encephalitis, and as more recently observed in North America, West Nile fever.

Dengue fever is an acute infectious disease characterized by biphasic fever, headache, pain in various parts of the body, prostration, rash, lymphadenopathy and leucopenia (Holstead, S B, 1980, Immunological parameters of togavirus disease syndromes, p. 107-173, in R W Schlesinger (ed.) The Togaviruses, Academic Press, Inc., NY; Sabin, A B, 1959, Dengue, p. 361-373, in T Rivers and F Horsfall (eds.), Viral and Rickettsial Infections of Man, JB Lippincott Co., Philadelphia).

Dengue is mosquito-borne and caused by four serologically related viruses known as dengue virus type 1 to type 4 (dengue-1 to dengue-4). Infection with one dengue serotype provides lifelong immunity to that subtype, but no cross-protective immunity to the other serotypes. Thus, persons living in an area of endemic dengue can be infected with three, and possibly four, dengue serotypes during their lifetime. Illness ranges from unapparent infection to dengue fever or, in severe cases, potentially fatal dengue hemorrhagic fever/dengue shock syndrome (DHF/DSS).

Dengue hemorrhagic fever (DHF) is a severe febrile disease characterized by abnormalities of hemostasis and increased vascular permeability, which in some instances results in a hypovolemic shock syndrome, dengue shock syndrome (DSS) (World Health Organization: 1975. Technical Guides for Diagnosis, Treatment, Surveillance, Prevention and Control of Dengue Hemorrhagic Fever. World Health Organization. Geneva). The mechanism of DHF/DSS may vary in different cases. The major factors contributing to DHF/DSS may include viral virulence, patient health status and secondary infection of different serotype dengue virus.

Considering the urgent need for *flavivirus* vaccines, a novel alternative approach is needed. Theoretically, live attenuated vaccines elicit the most effective, long-term, virus-specific immunity, and inactivated virus vaccines, including recombinant subunit vaccines, provide the highest level of safety. The ideal vaccine would be the one that can produce the efficacy of a live vaccine and the safety of subunit vaccine. That goal was met in the development of the pseudoinfectious virus-like particle (PVLP) *flavivirus* vaccines described herein.

SUMMARY OF THE INVENTION

The inventions relates to materials and methods for making a *flavivirus* vaccine. That vaccine comprises a virus-like particle (VLP) that can infect a host cell, can replicate in that host cell to produce viral proteins that are recognized by the host immune system, but which cannot be packaged into infectious viral particles. The virus-like particles of interest contain a replicon that has all of the necessary genes to ensure replicon RNA production and production of the flaviviral proteins. Thus, a preferred replicon is one that contains all of the non-structural genes, the preM and E genes. However, the capsid gene is manipulated to ensure that capsid protein either is not made, or what is made cannot be used to make an infectious viral particle, and to ensure high level expression of the preM and E proteins. The virus-like particles of interest can infect a host cell, then multiple copies of the replicon are made in the cell and the replicon is expressed to product preM and E proteins. The preM and E proteins can be released from the cell or expressed at the surface of the cell, and thus the vaccine of interest elicits both a host humoral and cellular response.

Additional features and advantages of the present invention are described in, and will be apparent from, the following Detailed Description of the Invention and the figures.

BRIEF DESCRIPTION OF THE FIGURES

FIG. 1 depicts the architecture of a *flavivirus*.

FIG. 2 depicts the *flavivirus* genome, and translation and processing of the *Flavivirus* polyprotein. At the top is the viral genome with the structural (S) and nonstructural (NS) protein coding regions, the 5' cap, putative 3' secondary structure, and the 5' and 3' non-translated regions (NTR) indicated. Boxes below the genome indicate precursors and mature proteins generated by the proteolytic processing cascade. Mature structural proteins are indicated by shaded boxes, and the nonstructural proteins and structural protein precursors by open boxes. Contiguous stretches of uncharged amino acids are shown by black bars. Asterisks denote proteins with N-linked glycans but do not necessarily indicate the position or number of sites used. Cleavage sites for proteases are indicated. ORF is open reading frame.

Figure 3:
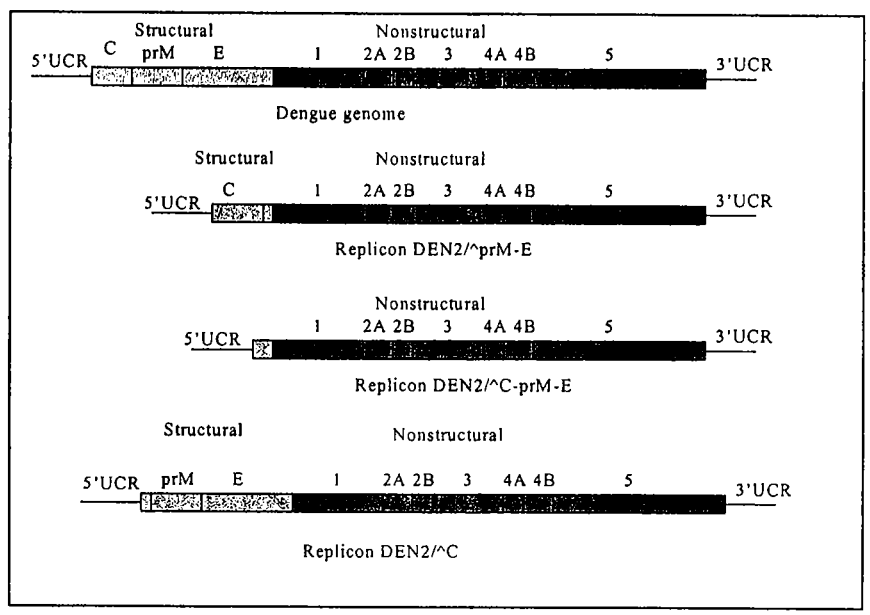

FIG. 3 diagrams the genome of dengue virus and derived replicons. The replicon DEN2/ΔprM-E was made from deletion of pre-membrane (prM) protein and envelope (E) protein from nucleotide 452 to nucleotide 2340. The replicon DEN2/ΔC-prM-E was made from deletion of nucleotide 157 to nucleotide 2340. The replicon DEN2/ΔC was made from deletion of nucleotide 160 to nucleotide 320. UCR is non-coding region.

Figure 4:
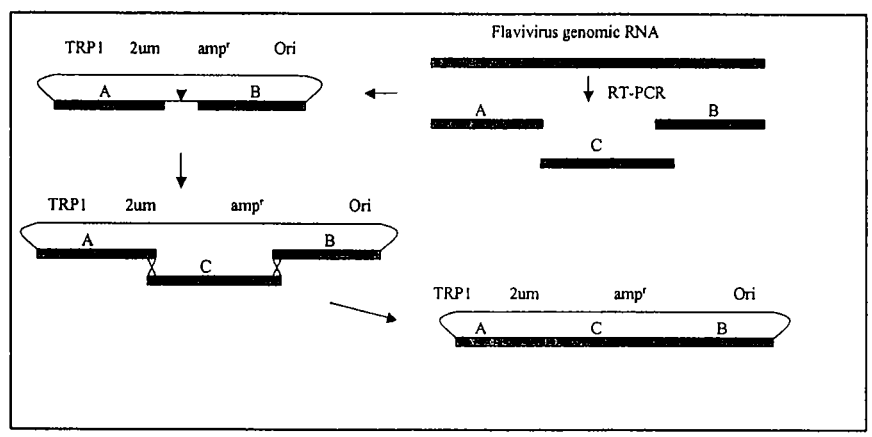

FIG. 4 depicts a protocol for making full length cDNA *flavivirus* clones using a shuttle vector system. TRP represents phosphoribosyl-anthranilate isomerase, a selectable marker gene of yeast; 2 μm represents the yeast origin of replication from that plasmid; amp is the ampicillin resistance gene; and ori represents a bacterial origin of replication. RT-PCR is reverse transcriptase polymerase chain reaction.

Figure 5:
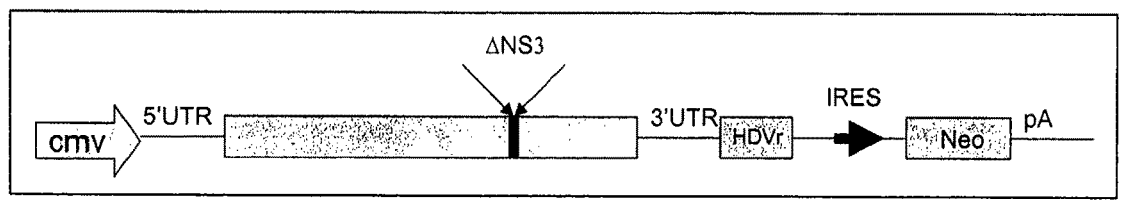

FIG. 5 depicts a construct of an NS3-deleted *flavivirus* subgenome expression plasmid. CMV is the cytomegalovirus promoter. UTR is an untranslated region. HDVr is described in the text. Neo is the neomycin resistance gene. pA is a polyadenylation site.

Figure 6:
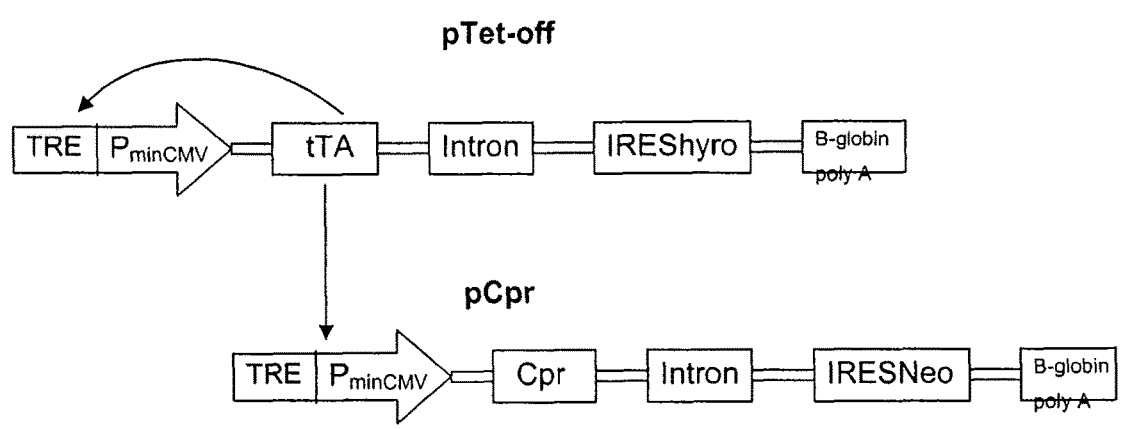

FIG. 6 depicts a scheme for production of construct. The pTet-off plasmid was used to generate a first stable cell line, BHK/Tet-off, autoregulatedly expressing the tetracycline transactivator (tTA). TRE, tetracycline-responsive element. $P_{minCMV}$, the minimal CMV promoter. tTA, tetracycline transactivator. IRES, internal ribosome entry site of encephalomyocarditis virus. Hyro, hygromycin B phosphotransferase gene. Neo, neomycin phosphotransferase gene. Intron is a synthetic sequence found in certain vectors of Clontech. Cpr is a polypeptide fragment that contains capsid protein and a segment of the pre portion of the premembrane protein.

DETAILED DESCRIPTION OF THE INVENTION

The *flavivirus* virion is composed of 6% RNA, 66% protein, 9% carbohydrate and 17% lipid (Russell P K, Brandt W E, Dalrymple J M, Chemical and Antigenic Structure of Flaviviruses, in Schlesinger R W, eds., The Togaviruses: Biology, Structure, Replication. New York: Academic; 1980: 503-529; and Trent D W, Naeve C W, Biochemistry and Replication, in Monath T, ed. St. Louis Encephalitis. Washington, D.C.: American Public Health Association; 1980 p. 159-199). An electron-dense nucleocapsid is composed of C (capsid) protein and genomic RNA. The envelope protein, E, and membrane (M) protein are embedded in the lipid bilayer by C-terminal hydrophobic anchors. However, immature particles found within intracellular vesicles contain exclusively unprocessed prM and are less infectious than released virions (Morens D M: Antibody-dependent enhancement of infection and the pathogenesis of viral disease. Clin Infect Dis 1994, 19:500-512).

The genome of flaviviruses is uniform, and is a single-stranded, positive-sense RNA molecule of about 10-11 kb, containing a single ORF constituting roughly 95% of the genome (Chambers T J, Hahn C S, Galler R, Rice C M: *Flavivirus* genome organization, expression, and replication, Ann Rev Microbiol 1990, 44:649-688). Genome-length RNAs appear to be the only virus-specific messenger RNA (mRNA) molecules in dengue-infected cells. On infection, the viral RNA is translated into a polyprotein of about 3400 amino acids that is processed into 10 gene products: the three structural proteins C, prM and E, and seven nonstructural (NS) proteins, 1, 2A, 2B, 3, 4A, 4B and 5 (Bhamarapravati N, Yokan S: Live attenuated tetravalent vaccine, in Gubler D J, Kuno G (eds.): Dengue and Dengue Hemorrhagic Fever. Wallingford, CAB International, 1997, pp 367-377; and Falgout, B and Markoff, L, 1995, The family flaviviridae and its diseases, p. 47-66. in: J S Porterfield (ed.), Exotic Viral Infections. Chapman and Hall Medical, London, United Kingdom).

As for all positive-stranded RNA virus, *flavivirus* genomic RNA is infectious. A focus of the instant invention is to manipulate the genome to produce replicons of a *flavivirus* that are defective in producing an infection, but continue to express those epitopes and determinants that can be recognized by the host, such as expressed by M and E genes.

For example, replicons can be constructed where portions or substantially all of the structural genes are deleted. Thus, some or all of C, prM and/or E can be removed. In the case of C, for example, nearly all of C, as few as only 20 remaining amino acids, can be removed without impacting replication and expression.

On the other hand, the instant invention relates to defective viral genomes that contain a majority of the structural proteins, or at the least, the majority of the polypeptide structures that are determinants for antibodies generated by the host. Thus, it is preferable that most of prM and E coding sequences are present as the proteins expressed thereby are the primary immunogenic sites in the wild-type virus infection. The C protein is less of a target for the host immune system so C would be the more favored target for manipulation to render the virus incapable of replication.

Thus, the C coding sequence can be deleted in part or in whole. The C coding sequence can be altered in other ways, such as with one or more point mutations, inversions, deletions and the like to ensure that the capsid protein is not expressed or the capsid protein that is expressed cannot be used to make a functional capsid for an infectious virus, without negatively impacting the expression of the preM and E coding sequences. Thus, a capsid can be made that contains additional expressed amino acids that prevent the protein from either folding properly or from being able to make the proper shell for the replicon.

Various dengue replicons were constructed as shown in FIG. 3, which have varying deletions and modifications of the structural genes. When introduced into host cells by electroporation, replicon replication occurred and expression occurred. The particle of interest is one which when made as taught in the instant invention yields an infectious particle but containing a defective replicon that cannot be packaged into infectious particles in host cells. Thus, a particle of interest infects once, the replicon is replicated and expressed, but the replicon is not packaged into particles.

A favored type of vector would be of the nature and structure as the one depicted in the lowermost diagram of FIG. 3, wherein only C is rendered non-expressible. Because of the similarity of genomic structures among the flaviviruses, that same approach is taken with other serotypes, strains and species of *flavivirus*, such as Japan encephalitis, West Nile virus and yellow fever.

*Flavivirus* infectious clones can be unstable in *Escherichia coli*. That hurdle can be overcome by using eukaryotic host cells such as *Saccharomyces cerevisiae*. Shuttle vectors using dengue virus infectious full-length clones have been made (Polo, S, Ketner, G, Levis, R and Falgout, B, 1997, Infectious RNA transcriptions from full-length dengue virus type 2 cDNA clones made in yeast. J Virol 71:5366-5374;

Pang, X and Markoff, L 1998, A full-length "infectious" cDNA clone of a dengue serotype 2 vaccine virus. Poster, Fifth International Symposium on Positive Strand RNA viruses. p. 1-73; and Pur, B, Polo, S, Hayes, C, Falgout, B, 2000, Construction of full length infectious clone for dengue-1 virus western pacific 74 strain. Virus Genes, 2000: 20(1): 57-63). The shuttle vector contains a bacterial replication origin and selectable marker, and a yeast replication origin and a yeast selectable marker.

Thus, to assist in the construction and scale up production of a PVLP of the instant invention, a scheme is constructed wherein cloning of the *flavivirus* 5' and 3' cDNA fragments lacking a central portion occurs in a polylinker of the shuttle vector, and then in yeast, a full-length cDNA clone is assembled by homologous recombination between the central cDNA fragment of the *Flavivirus* genome and the cloned 5' end and 3' end, as depicted in FIG. 4.

The replicon with some portion of the C gene deleted can express all major viral antigens and is most immunogenic of the replicons made and tested. The instant invention is related to developing a *flavivirus* replicon which when expressed, contains the most immunogenicity. Thus, a replicon of interest is one that contains most or all of the known viral antigens, one which has one or more defects that prevent viral infectivity yet enable continued RNA replication and expression within the host cells because the replicon cannot be packaged into VLP in host cells.

The replicon of interest also is one that does not necessarily contain a transgene as the purpose of the replicon is to produce preM and E protein. Thus, the replicon of interest is not one targeted to carrying foreign genes, that is, the replicon is not a cloning vector. Instead, a replicon of interest is targeted to contain as much of the *flavivirus* genome without being replication competent, and not containing any genes of another virus or another species of *flavivirus*. However, the replicon can be constructed to contain and express a molecule that can be used to enhance host recognition and reaction to the preM and E proteins. Thus, the replicon can be configured to contain, for example, an adjuvant or any other molecule that enhances immunogenicity.

Moreover, changes can be made to the preM and E coding sequences to ensure or to enhance immunogenicity of same. Thus, point mutations and the like can be made in the preM and E coding sequences so that when expressed in a host, the expressed proteins result in an immunoprotecting response.

With that in mind, there are several methods available to the artisan to package the replicon of interest into a virus-like particle. Generally, the strategies employ the use of additional vectors or packaging cells that provide the necessary components in trans that can complement the defective replicon to enable packaging into a particle.

Thus, another goal of the instant invention is to develop a packaging system for a *flavivirus* replicon. For example, a Sindbis replicon capable of expressing dengue structural proteins prM, E and C was constructed. When the Sindbis replicon transfected cells twenty-four hours after defective dengue replicon transfection, dengue replicon RNA was encapsidated in "virus-like" particles (VLPs) and released in culture medium.

Thus, replicon RNA can be packaged into a VLP when structural proteins are supplied in trans using an appropriate packaging cell containing the appropriate complementing expression products.

Since the replicon containing VLP is infectious, but cannot produce infectious virions from the infection, because, for example, proper capsid proteins are not expressed in the infected host cell, the VLP is named as a "pseudoinfectious virus-like particle (PVLP) or a non-replicating particle. Thus, a non-replicating particle is one that infects a host cell, but that host cell does not yield infectious virus particles resulting from that infection. For the purposes of the instant invention and the teachings herein, PVLP and VLP are synonymous.

The unique character of the PVLP makes the PVLP a source for effective and safe *flavivirus* vaccines. A highly immunogenic viral strain of PVLP should mimic the process of natural infection of a *flavivirus* and produce long-lasting immunity. Thus, a preferred PVLP of interest is one that contains the genetic material to express all of the epitopes expressed by the wild-type prM and E proteins, and perhaps, C as well. If manipulations are to be made to the structural proteins to ensure replication incompetence, changes should be made to the C protein, and a lesser amount of change is preferred.

The first embodiment of a packaging system uses two consecutive infections: first with a *Flavivirus* PVLP, and 24 hours later, with a Sindbis PVLP that provides *Flavivirus* structural proteins in trans, as described in further detail below. The development of alphavirus packaging cell lines has been described (Polo, J M, Belli, B, Driver, D, Frolov, I, Sherrill, S, Hariharan, M J, Townsend, K, Perri, S, Ment, S J, Jolly, D J, Chang, S W, Schlesinger, S and Dubensky, Jr., T, 1999. Stable alphavirus packaging cell lines for Sindbis virus-derived vectors and Semliki forest virus-derived vectors. Proc Natl Acad Sci USA Vol 96:4598-4603). The Sindbis virus packaging cell line of interest employs two expression cassettes each containing a part of the structural genes. Some modifications can be made to facilitate the construction of cassettes and to enhance packaging efficiency.

*Flavivirus* PVLP infect up to 100% of susceptible cells following appropriate titration. Vero cells in a six-well dish are infected with PVLP at serial dilution. About 24 hours post-infection, packaging Sindbis PVLP are added into each six-well dish, and agitated in a rocker platform for 2 hours at 37° C., and then the unattached Sindbis PVLP were washed out with culture medium. Cell culture fluid is collected at 48 hours after the second infection and treated with Sindbis-specific polyclonal antibodies to remove possible contaminants of replicative-competent Sindbis particles.

To prepare partially purified PVLP, culture fluid is clarified by centrifugation at 16,000×g in a microcentrifuge for 15 min at 40° C., and the particles are pelleted from the supernatant fluid by ultracentrifugation at 40,000 rpm for 2 hours at 40° C. in the AH650 rotor of a Sorvall OTD55B centrifuge. The pellets are resuspended in 50 µl of PBS and left to dissolve overnight at 40° C. To determine the titer of the dengue PVLPs, BHK-21 cells on eight-well chamber slides are infected with 50 µl of serial 10-fold dilutions of cell culture fluid or of resuspended pelleted material for 2 hours at 37° C. The fluid then is replaced with 1 ml of Dulbecco's minimal essential medium supplemented with 2% fetal bovine serum. Cells are incubated for 24 hours at 37° C. in a $CO_2$ incubator and subjected to immunofluorescence (IF) analysis with a 1:100 dilution of HMAF as described below.

The second embodiment of a packaging cell line is based on a mammalian gene expression system. The eukaryotic expression plasmid pCI-neo (Promega) is used for the expression of structural protein C-pr (pr represents the pr segment of prM), due to its high expression rate (Almond, B D and Schenborn, E T, A comparison of pCI-neo vector and pcDNA4/HisMax vector. Promega Publication). The pCI-neo mammalian expression vector contains a CMV IE enhancer/promoter, an optimized chimeric intron and the simian virus 40 (SV40) late polyadenylation signal. Those three elements combine to yield strong, constitutive expression of the cloned gene in mammalian cells. For example, as to dengue virus type 2 strain, the gene fragment encoding aa 1 to 205 (nt 93-640) of the dengue-2 NGC strain virus structural protein C and pr is PCR amplified using the sense primer and the antisense primer, with dengue-2 cDNA as the template. Unique restriction sites, XhoI and XbaI, are created in the primers. The PCR product as well as pCI vector are digested with XhoI and XbaI, and then purified by Qiagen column. The purified XhoI/XbaI-digested PCR product and pCI fragments are ligated to form the pCI-C plasmid. The plasmid DNA from the selected clone is purified by Qiagen column. The sequence of protein C gene is confirmed by DNA sequencing. After BHK-21 cells are transfected with pCI-C by electroporation, individual clones of G418-resistant cells are selected by limited dilution in a 96-well dish. Dengue-2 replicon with the protein gene C gene deleted can be used to transfect the cloned cells, and culture fluid collected to determine the packaging ability of each clone as described above. Favored packaging cell lines are those that produce the highest levels of virus-like particles free from replication-competent virus.

The third embodiment of a packaging cell line is based on the tetracycline induced gene expression system. The system is commercially available from Clontech in Tet-On and Tet-Off formulations, allowing induction of gene expression either by addition or by the removal of tetracycline, see Clontech manuals for a depiction of the constructs. The Tet-Off system was chosen to avoid the presence of antibiotic in PVLP preparations. To generate a packaging cell line that allows tetracycline-inducible expression of the *flavivirus* structural gene cassette (Cpr), a BHK cell line, BHK-Tet-Off, stably expressing the tetracycline transactivator was established. Thus, BHK21 cells were transfected with a pTet-off plasmid DNA. Two days following transfection, the antibiotic G418 (Sigma) was added at a concentration of 200 μg/ml for selection of cell clones. Cell clones were isolated and cultured successfully from this transfection. These clones were then analyzed for induction of expression by transfection with the plasmid, pTRE2luciferase (Clontech), in the presence (0.5 μg/ml) or absence of doxycycline (an antibiotic of the same spectrum as tetracycline but with higher specific activity and a longer half-life). The BHK-Tet-Off cell clone displaying the highest fold induction of luciferase expression compared to uninduced cells were used to establish a stable BHK cell line expressing the *flavivirus* structural gene cassette Cpr. The cells were transfected with pTRECpr plasmid DNA constructed by cloning the PCR fragment of a *flavivirus* Cpr gene and pTK-Hyg plasmid. Transfected cells were subjected to selection with 10 μg/ml of hygromycin in medium that also contained 200 μg/ml of G418 and 0.5 μg of doxycycline/ml. To select the most efficient packaging cell line, a number of cell clones conferring resistance to G418 and puromycin were electroporated with a *flavivirus* replicon RNA and cultured without doxycycline to determine whether they were able to produce PVLPs. The titers of PVLPs (in infectious units [IU] per milliliter) present in harvested culture fluids (CFs) were determined by infection of Vero cells followed by immunofluorescence analysis with mouse hyperimmune acidic fluid. The most efficient cell clone was used for PVLP production.

In another embodiment, as a variant of the tetracycline inducible system, two sets of bicistronic expression vectors, pTet-off and pCpr (FIG. 6), were constructed for increasing the stability of the packaging cell line and reducing the required numbers of screening cells. The autoregulated expression plasmid, pTet-off, was constructed with a tetracycline-regulatable promoter, $P_{hCMV*\text{-}1}$ (from plasmid pTRE2 of Clontech), and followed by bicistronic expression cassette of the tetracycline-responsive transcriptional activator (tTA) and hygromycin B phosphotransferase ($Hyg^r$). The autoregulatory tTA expression vector allows higher levels of tTA expression when induced, while minimizes the toxic effect of tTA by keeping low level expression of tTA with doxycycline.

Plasmid pCpr was constructed with the promoter $P_{hCMV*\text{-}1}$ followed by a bicistronic expression cassette of C-pr and Neomycin phosphotransferase ($Neo^r$).

BHK/Tet-off cells were developed by transfection of BHK-21 cells with plasmid pTet-off, and subjected to selection with 0.4 mg/ml of hygromycin B and 0.5 μg/ml of doxycycline. Ten clones were analyzed for inducible expression by transfection with plasmid pTRE2EGFP (Clontech), in the presence (0.5 μg/ml) or absence of doxycycline. All clones showed some degree of inducibility for EGFP expression. The cell clone with highest inducible production of EGFP was used to establish a stable BHK cell line to express dengue protein, C-pr. The cells were transfected with plasmid pCpr and subjected to selection with 0.2 mg/ml G418 and 0.3 mg/ml of hygromycin B, as well as 0.5 μg/ml of doxycycline. To select the most efficient packaging cell line, fifteen cell clones were electroporated with replicon DEN2/ΔC (a clone with deletion in the C coding sequence from nucleotide 160 through 320) RNA and cultured in medium without doxycycline.

The titers of replicon VLP (in infectious units (IU) per milliliter) present in harvested culture fluids (CFs) were determined by infection of LLC-MK2 cells followed by indirect immunofluorescence analysis (IF) with dengue type 3 hyperimmune mouse ascitic fluid (HMAF). Ten of 15 clones produced replicon VLPs. The most efficient cell clone, BHK/C-pr/8, producing $4.6\times10^6$ IU of replicon VLPs.

The fourth embodiment of a packaging cell line is based on transcomplementation of defective *flavivirus* genomic RNAs with a large lethal deletion in the C-terminal region of a nonstructural gene, such as NS3.

The plasmid was prepared by replacing the SP6 promoter in the full-length clone described above with the cytomegalovirus (CMV)-derived immediate-early enhancer/promoter region. The fragment containing the CMV sequence followed by the 5' end of the *flavivirus* sequence was produced in a fusion PCR. The hepatitis delta virus antigenomic ribozyme (HDVr) sequence was inserted immediately downstream of the last nucleotide of the *flavivirus* sequence. The encephalomyelocarditis virus internal ribosome entry site (IRES) sequence and neomycin resistance gene (ORF) were added for selection. BHK21 cells were transfected with the plasmid DNA. Two days following transfection, the antibiotic G418 (Sigma) was added at a concentration of 200 μg/ml for selection of cell clones. Cell clones were isolated and cultured successfully from this transfection. To select the most efficient packaging cell line, a number of cell clones conferring resistance to G418 and puromycin were electroporated with *flavivirus* replicon RNA to determine whether they were able to produce PVLPs. The titers of PVLPs (in infectious units [IU] per milliliter) present in harvested culture fluids (CFs) were determined by infection of Vero cells followed by immunofluorescence analysis with mouse hyperimmune acidic fluid. The most efficient cell clone was used for PVLP production.

To further facilitate the formation of virus-like particles (VLP), amino acid insertions and substitutions (for example, the VPQAQA (SEQ ID NO:1) mutation) at the COOH terminus of the prM signal sequence can be used (see FIG. 3, uppermost diagram, the VPQAQA (SEQ ID NO:1) mutation could be inserted at residues 109-114 at the juncture of the C and prM domains). The VPQAQA (SEQ ID NO:1) sequence is one that is known to enhance signal peptidase cleavage. The insertion facilitates efficient signal peptidase cleavage of the prM protein from its dependence on cleavage in the cytoplasm by the viral NS2B-3 protease. The result is enhanced packaging and packaging efficiency.

Flavivirus RNA replicons were encapsidated into a PVLP by a procedure involving two consecutive electroporations of cells, first, for example, with flavivirus replicon RNA and about twenty-four hours later with a recombinant Sindbis virus replicon RNA expressing transcomplementing flavivirus structural proteins. Once the flavivirus PVLPs are obtained, the first cell electroporation by the flavivirus replicon RNA can be replaced by an infection of the PVLP. The use of Sindbis to deliver flavivirus genes in trans has been used in the production of picornovirus (e.g. poliovirus) replicon PVLPs with the necessary structural proteins in trans using a vaccinia vector (Porter, D C, Wang, J, Moldoveanu, Z, McPherson, S and Morrow, C, 1997. Immunization of mice with poliovirus replicons expressing the C-fragment of tetanus toxin protects against lethal challenge with tetanus toxin. Vaccine 15:257-264).

Both humoral antibody and cellular immune responses are implicated in protection and recovery from flavivirus infection. The flavivirus replicon-based vaccine of interest induces both arms of the immune response. The particles are composed of preM and E proteins and thus, the particles themselves are immunogens. But the particles of interest infect host cells, and in those cells, additional preM and E proteins are expressed. The preM and E proteins either can be released from those cells, providing additional antigenic stimuli to the host, or can be expressed at the infected host cell surface, for example, on host antigen presenting cells, to provide yet another antigenic stimulus to the host.

The vaccine replicons contain the viral antigens, including structural proteins prM and E, and optionally can express nonstructural protein NS1. Previous reports demonstrated that those viral proteins induce a protective immune response (Heinz, F X & Roehrig, J, 1990, in Immunochemistry of Viruses, Vol II. Amsterdam-NY-Oxford, Elsvier, p. 289-305; Heinz F X, 1986, Epitope mapping of flavivirus glycoproteins. Adv Virus Res 31:103-168; Bray, M and Lai, C J, 1991, Dengue virus premembrane and membrane proteins elicit a protective immune response. Virology, 185: 505-508; Henchal E A, Henchal, L S and Shlesinger, J J, 1988, Synergistic interactions of anti-NS1 monoclonal antibodies protect passively immunized mice from lethal challenge with dengue 2 virus. J. Gen Virol. 69:2101-2107; and Schlesinger J J, Brandriss, M W, Cropp, C B et al., 1986. Protection against yellow fever in monkeys by immunization with yellow fever virus non-structural protein NS1. J Virol 60:1153-1155).

Suitable models for testing the efficacy of a pharmaceutical composition of interest exist as there are animal models that simulate flavivirus infection. For example, a protocol used for immunization of mice and subsequent challenge with dengue virus has been described (Bray, M, Zhao, B, Marckoff, L, Eckels, K, Chanock, R M and Lai, C, 1989, Mice immunized with recombinant vaccinia virus expressing dengue 4 virus structural proteins with or without nonstructural protein NS1 are protected against fatal dengue encephalitis. J. Virol. 63:2853-2856). Briefly, in 10 mice for each group, female BALB/c mice are immunized at 3 weeks of age (day 1) and again on day 14 by intraperitoneal inoculation of the virus-like particles. Control animals receive phosphate-buffered saline (PBS). All animal are bled on day 0 and day 21. Mice are challenged on day 22 by intracerebral injection of 100 times the 50% lethal dose ($LD_{50}$) of dengue virus. Following challenge, mice are observed for 21 days for signs of encephalitis, and the number of mice with any important symptoms (encephalitis, paralysis and death) are recorded daily. Sera also are collected from survivors for comparison with prechallenged sera.

The dose of each VLP is determined. The seroresponse of immunized mice to individual dengue virus proteins is analyzed by radioimmunoprecipitation of [$^{35}$S] methionine-labeled dengue virus antigens using commercially available labeling kits and antibodies. The plaque reduction assay is used to measure titers of dengue-specific neutralizing antibodies in mouse sera. Approximately 0.5 ml of a serum sample to be used in the assay first is heat inactivated by incubation for 30 min at 56° C. Fourfold dilutions of serum in a final volume of 0.3 ml, starting at 1:10 dilution, are prepared using medium M199 with 2% heat-inactivated FBS as a diluent. To each 0.3 ml aliquot of diluted serum is added an equal volume of medium containing 150-180 PFU of dengue virus. Virus and serum are mixed and incubated for 30 min at 37° C. In each assay, a no serum control and controls consisting of each dengue type-specific mouse hyperimmune ascitic fluid (ATCC) at two dilutions are also included. Virus-serum and control mixtures are plated on confluent monolayers of LLC-MK2 cells in Costar six-well plates (Corning Inc., Corning, N.Y.) at 0.2 ml/well. Duplicate wells are infected for each sample. Virus adsorption is carried out for 1 hour at room temperature with manual rocking every 15 min. Wells then are overlaid with medium containing 1% agarose (SeaKem LE; BioWhittaker, Rockland, Me.) in Earle's balanced salt solution plus 10% FBS with added essential vitamins and amino acids (Invitrogen) at 6 ml/well. Plates are incubated for 7 days at 37° C. in 5% $CO_2$. Wells are then overlaid with 4% neutral red solution (4 ml of neutral red solution plus 96 ml of PBS) containing 1% agarose. Plates are incubated for 24 hours at 37° C. The average of plaque counts is used to calculate the 50% reduction in plaque number level.

An exemplified embodiment is a dengue vaccine that is tetravalent, one that immunizes a host to dengue types 1, 2, 3 and 4.

Because the flaviviruses have a unified generic genetic structure, the goal of having a tetravalent vaccine is achieved by the use of replicons as taught herein for each of the types 1, 2, 3 and 4. Moreover, the method of making a vaccine as taught herein using two vectors carrying the flavivirus structural genes and a packaging cell carrying a gene encoding an overlapping peptide that in yeast following homologous recombination reconstitutes the whole of the flavivirus structural genes, has application not only to dengue virus but also to all flavivirus species as well.

The PVLP of interest is incorporated into pharmaceutical compositions suitable for administration to serve as a vaccine, as known in the vaccine art. Such compositions typically comprise the active ingredient and a pharmaceutically acceptable carrier. As used herein, the language "pharmaceutically acceptable carrier" is intended to include any and all solvents, dispersion media, coatings, antibacterial and antifungal agents, isotonic and absorption delaying agents and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds also can be incorporated into the compositions.

A pharmaceutical composition of the invention for use as disclosed herein is formulated to be compatible with the intended route of administration. Examples of routes of administration include parenteral, e.g., intravenous, intradermal, subcutaneous, oral (e.g., inhalation), transdermal (topical), transmucosal and rectal administration. Solutions or suspensions used for parenteral, intradermal or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as EDTA; buffers such as acetates, citrates or phosphates and agents for the adjustment of tonicity such as sodium chloride or dextrose. pH can be adjusted with acids or bases, such as HCl or NaOH. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL® (BASF; Parsippany, N.J.) or phosphate-buffered saline (PBS). In all cases, the composition must be sterile and should be fluid to the extent that easy syringability exists. The composition must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol and liquid polyethylene glycol and the like) and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal and the like. In many cases, it will be preferable to include isotonic agents, for example, sugars, polyalcohols such as mannitol, sorbitol or sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze drying that yield a powder of the active ingredient plus any additional desired ingredient from a previously sterile-filtered solution thereof.

Oral compositions generally include an inert diluent or an edible carrier. The composition can be enclosed in gelatin capsules or compressed into tablets. For the purpose of oral therapeutic administration, the active compound can be incorporated with excipients and used in the form of tablets, troches or capsules. Oral compositions also can be prepared using a fluid carrier to yield a syrup or liquid formulation, or for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate or orange flavoring.

For administration by inhalation, the compound is delivered in the form of, for example, an aerosol spray from a pressurized container or dispenser that contains a suitable propellant, e.g., a gas such as carbon dioxide or a nebulizer, or a mist.

Systemic administration also can be by transmucosal or transdermal means. For transmucosal or transdermal administration, penetrants appropriate to the barrier to be permeated are used in the formulation. Such penetrants generally are known in the art and include, for example, for transmucosal administration, detergents, bile salts and fusidic acid derivatives. Transmucosal administration can be accomplished through the use of nasal sprays or suppositories. For transdermal administration, the active compounds are formulated into ointments, salves, gels or creams as generally known in the art.

The vaccine also can be prepared in the form of suppositories (e.g., with conventional suppository bases such as cocoa butter and other glycerides) or retention enemas for rectal delivery.

In one embodiment, the active compound is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid.

Methods for preparation of such formulations will be apparent to those skilled in the art. The materials also can be obtained commercially from Alza Corporation and Nova Pharmaceuticals, Inc.

Liposomal suspensions (including liposomes targeted with monoclonal antibodies and other such targeting molecules) also can be used as pharmaceutically acceptable carriers. Those can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The dosages, for example, preferred route of administration and amounts, are obtainable based on empirical data obtained from preclinical and clinical studies, practicing methods known in the art. For repeated administrations over several days or longer, depending on the condition, the treatment is sustained until a desired suppression of disease symptoms occurs. However, other dosage regimens may be useful. The progress of the therapy is monitored easily by conventional techniques and assays. An exemplary dosing regimen is disclosed in WO 94/04188. The specification for the dosage unit forms of the invention is dictated by and directly dependent on the unique characteristics of the active compound and the particular therapeutic effect to be achieved and the limitations inherent in the art of compounding such an active compound for the treatment of individuals.

The pharmaceutical compositions can be included in a container, pack or dispenser together with instructions for administration.

Another method of administration comprises the addition of a compound of interest into or with a food or drink, as a food supplement or additive, or as a dosage form taken on a prophylactic basis, similar to a vitamin. The peptide of interest can be encapsulated into forms that will survive passage through the gastric environment. Such forms are commonly known as enteric-coated formulations. Alternatively, the peptide of interest can be modified to enhance half-life, such as chemical modification of the peptide bonds, to ensure stability for oral administration, as known in the art.

All references cited herein are herein incorporated by reference in entirety.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

The invention is claimed as follows:

1. A stable packaging cell that expresses a Dengue Cpr protein, wherein C is a capsid protein and pr is a segment of the pre portion of premembrane (prM) protein, suitable for releasing pseudoinfectious Dengue virus-like particles from said cell.

2. The stable packaging cell of claim 1, further comprising a Dengue replicon that expresses Dengue prM and E proteins and said Dengue replicon cannot express a Dengue C protein or expresses a Dengue C protein that cannot comprise the capsid of an infectious Dengue virus particle.

3. The stable packaging cell of claim 1 that does not express one or more of a Dengue premembrane (prM) protein, a membrane (M) protein or an envelope (E) protein.

4. The stable packaging cell of claim 1 that does not express a Dengue premembrane (prM) protein or a membrane (M) protein; and an envelope (E) protein.

5. The stable packaging cell of claim 1, further comprising a replicon that expresses at least one Dengue immunogen.

6. The stable packaging cell of claim 5, further comprising a Dengue pseudoinfectious virus-like particle.

7. The stable packaging cell of claim 5 with a Dengue pseudoinfectious virus-like particle on the surface thereof.

8. A composition comprising the stable packaging cell of claim 1 and a Dengue pseudoinfectious virus-like particle.

9. A method of making a pseudoinfectious Dengue virus-like particle, comprising further transforming the stable packaging cell of claim 1 with a replicon that expresses at least one Dengue immunologic determinant and does not express Dengue C protein, and obtaining said pseudoinfectious Dengue virus-like particle from said transformed stable packaging cell.

\* \* \* \* \*